United States Patent
De Magistris et al.

(10) Patent No.: US 10,556,346 B2
(45) Date of Patent: Feb. 11, 2020

(54) INSPECTING CLEARANCE SIZE BETWEEN MECHANICAL PARTS

(71) Applicant: INTERNATIONAL BUSINESS MACHINES CORPORATION, Armonk, NY (US)

(72) Inventors: Giovanni De Magistris, Kawasaki (JP); Tadanobu Inoue, Yokohama (JP); Asim Munawar, Ichikawa (JP)

(73) Assignee: International Business Machines Corporation, Armonk, NY (US)

( * ) Notice: Subject to any disclaimer, the term of this patent is extended or adjusted under 35 U.S.C. 154(b) by 194 days.

(21) Appl. No.: 15/607,738

(22) Filed: May 30, 2017

(65) Prior Publication Data

US 2018/0345503 A1 Dec. 6, 2018

(51) Int. Cl.
*B25J 9/16* (2006.01)
*B07C 5/342* (2006.01)
*B25J 18/06* (2006.01)
*G01N 21/95* (2006.01)

(52) U.S. Cl.
CPC .............. *B25J 9/1697* (2013.01); *B07C 5/342* (2013.01); *B25J 9/1615* (2013.01); *B25J 18/06* (2013.01); *G01N 21/9515* (2013.01)

(58) Field of Classification Search
CPC ........ B25J 9/1697; B25J 18/06; B25J 9/1615; B25J 9/1633; B25J 9/1666; B25J 9/1676; B25J 9/1687; B25J 11/007; G01N 21/9515; G01N 21/88; B07C 5/342; G05B 2219/40031; G05B 2219/40032; G05B 2219/40087; G05B 2219/35223; G05B 2219/39084; G05B 2219/45055; G05B 2219/45064; G05B 2219/45067
See application file for complete search history.

(56) References Cited

U.S. PATENT DOCUMENTS

| | | | |
|---|---|---|---|
| 5,070,302 A | 12/1991 | Marcus | |
| 7,313,464 B1 | 12/2007 | Perreault | |
| 7,996,197 B1 | 8/2011 | Xavier | |
| 8,364,454 B2 | 1/2013 | Arbitter et al. | |
| 8,892,242 B2 | 11/2014 | Kimura | |
| 2011/0225787 A1* | 9/2011 | Sato | B25J 9/1687 29/407.01 |
| 2013/0325030 A1 | 12/2013 | Hourtash | |
| 2015/0066443 A1 | 3/2015 | Chang et al. | |
| 2017/0014995 A1* | 1/2017 | Kato | B25J 13/085 |

FOREIGN PATENT DOCUMENTS

JP 2005205501 A 8/2005

* cited by examiner

*Primary Examiner* — Adam R Mott
(74) *Attorney, Agent, or Firm* — Jordan T. Schiller (57) ABSTRACT

A computer-implemented method for inspecting a clearance size between a hole and an object inserted in the hole, includes: controlling a robot arm so that the robot arm performs a predetermined motion to move the object inserted in the hole; monitoring a response to the predetermined motion from the hole and the object; and calculating information on the clearance size between the hole and the object using the response to the predetermined motion.

15 Claims, 8 Drawing Sheets

INSPECTING CLEARANCE SIZE BETWEEN MECHANICAL PARTS

BACKGROUND

The present invention relates to inspecting a clearance size between mechanical parts.

There are many cases in which we would like to get the size of actual clearance between mechanical parts. For example, there is a case that manufacturers would like to avoid looser clearance than a threshold at a fitting assembly process in a factory line. Although they can avoid looser clearance by using mechanical parts with tight tolerance to the designed size, it would make the parts' cost higher. A laser scanner can be utilized to measure the actual size precisely, but it is too time-consuming to measure each mechanical part at a fitting assembly process in a factory line.

SUMMARY

According to an embodiment of the present invention, there is provided a computer-implemented method for inspecting a clearance size between a hole and an object inserted in the hole. The method includes controlling a robot arm so that the robot arm performs a predetermined motion to move the object inserted in the hole. The method further includes monitoring a response to the predetermined motion from the hole and the object. The method further includes calculating information on the clearance size between the hole and the object using the response to the predetermined motion.

According to another embodiment of the present invention, there is provided a robot system. The robot system includes a robot arm, a controller, a monitor, and a calculator. The robot arm is configured to hold an object to insert the object in a hole provided in a first object. The controller is configured to control the robot arm so that the robot arm performs a predetermined motion to move the object inserted in the hole. The monitor is configured to monitor a response to the predetermined motion from the hole and the second object. The calculator is configured to calculate information on a clearance size between the hole and the object.

According to yet another embodiment of the present invention, there is provided a computer program product for inspecting a clearance size between a hole and an object inserted in the hole. The computer program product includes a computer readable storage medium having program instructions embodied therewith. The program instructions are executable by a computer to cause the computer to control a robot arm so that the robot arm performs a predetermined motion to move the object inserted in the hole. The program instructions are executable by a computer to cause the computer to monitor a response to the predetermined motion from the hole and the object. The program instructions are executable by a computer to cause the computer to calculate information on the clearance size between the hole and the object using the response to the predetermined motion.

DETAILED DESCRIPTION

Hereinafter, exemplary embodiments of the present invention will be described in detail with reference to the attached drawings.

It is to be noted that the present invention is not limited to these exemplary embodiments to be given below and may be implemented with various modifications within the scope of the present invention. In addition, the drawings used herein are for purposes of illustration, and may not show actual dimensions.

Figure 1:
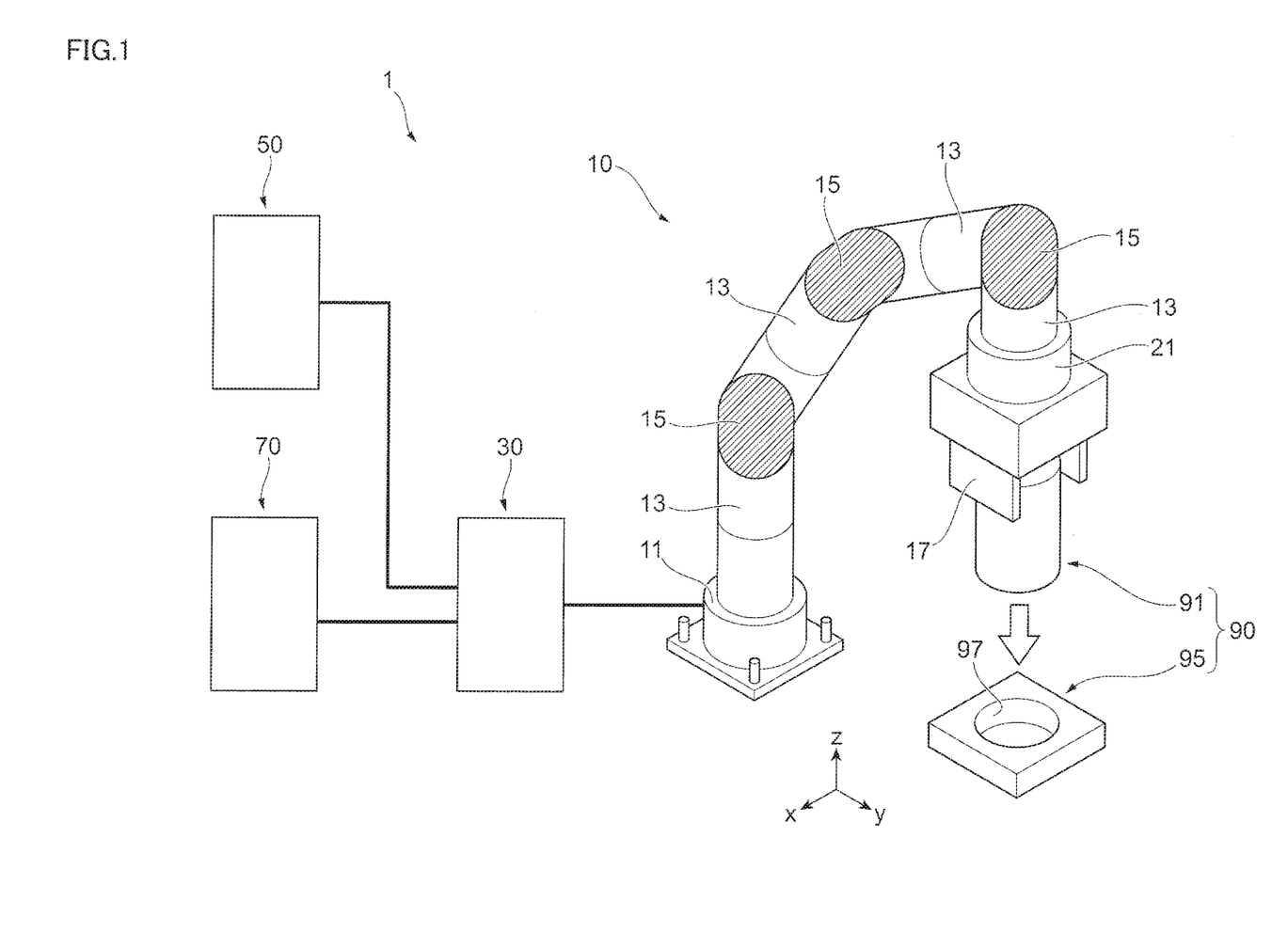
FIG. 1 depicts a schematic view of a configuration of a robot system according to an exemplary embodiment of the present invention.

FIG. 1 depicts a schematic view of a configuration of a robot system 1 according to an exemplary embodiment of the present invention.

The robot system 1 is configured to manipulate work pieces (mechanical parts) 90. In the shown example, the work pieces 90 may include a shaft (peg) 91, and a body part 95 provided with a hole (recess) 97. The robot system 1 holds the shaft 91 and inserts it in the hole 97 (refer to a white arrow in FIG. 1). The shaft 91 is an example of a claimed object.

As shown in FIG. 1, the robot system 1 may include a robot arm 10, a controller 30, an operating device 50, and an external device 70. The configuration of the controller 30, the operating device 50, and the external device 70 will be described with FIG. 2 later.

The robot arm 10 may include a base 11, arms 13, joints 15, a gripper 17, and a wrist sensor 21. The base 11 supports one of the arms 13. The arms 13 are linked with each other by the respective joints 15. The gripper 17 is provided at the end of the linked arms 13. The gripper 17 holds and releases the shaft 91.

The wrist sensor 21 is a six-axis force-torque sensor. The wrist sensor 21 may measure three force components along x, y, and z axes as well as their corresponding moments and/or torques. In other words, the wrist sensor 21 may detect the motion of the gripper 17 (the shaft 91) in 6 degrees of freedom.

In the shown example, the wrist sensor 21 is provided nearby the gripper 17. More specifically, the wrist sensor 21 is provided between the gripper 17 and the joint 15 nearest to the gripper 17. Note that the wrist sensor 21 is provided on the position where a relative position of the wrist sensor 21 with respect to the gripper 17 is maintained regardless of the movement of the arms 13.

Figure 2:
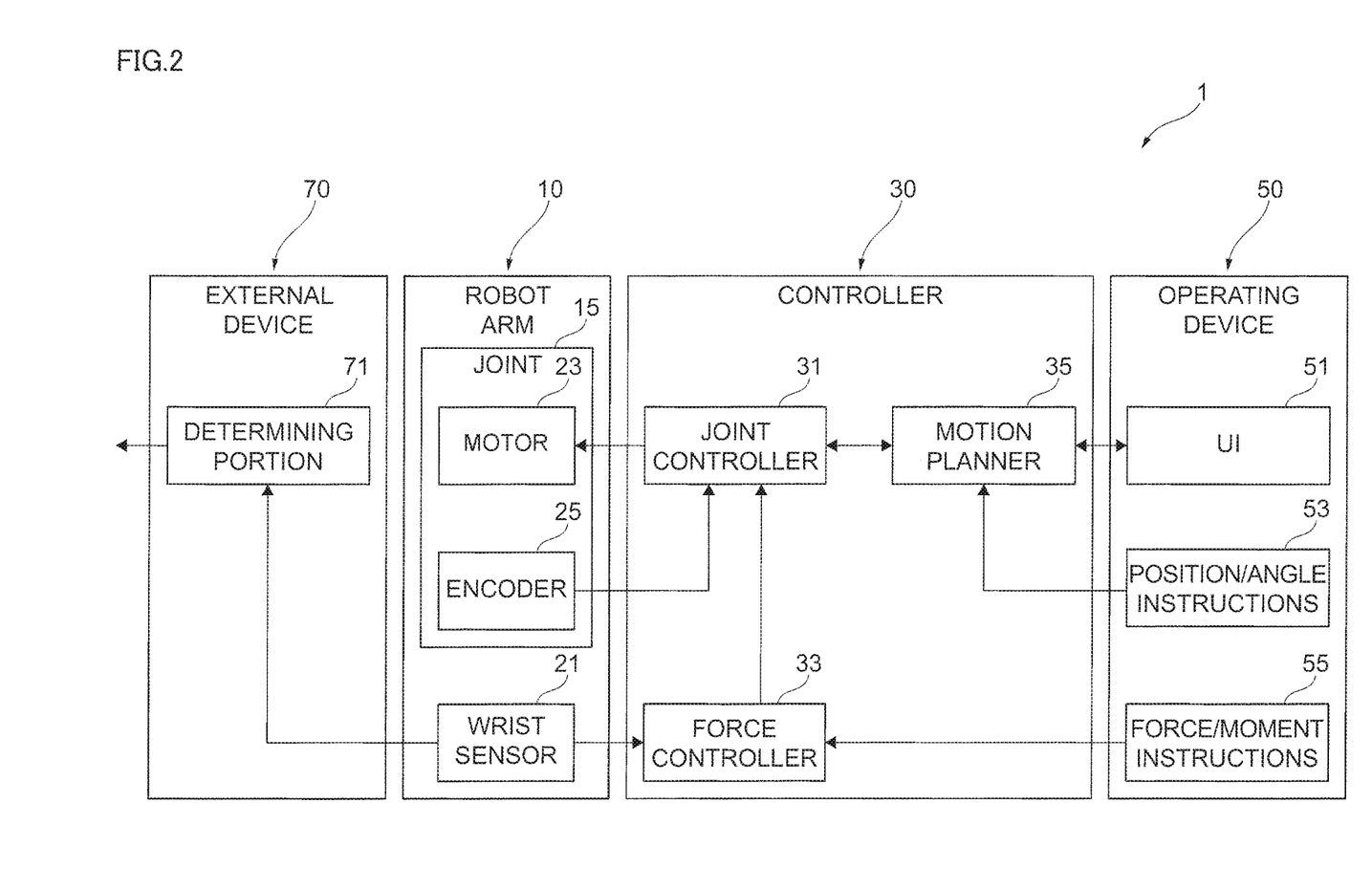
FIG. 2 depicts a block diagram showing a configuration of the robot system according to the exemplary embodiment.

FIG. 2 depicts a block diagram showing a configuration of the robot system 1 according to the exemplary embodiment. Referring to FIGS. 1 and 2, the configuration of the robot system 1 will be described.

As shown in FIG. 2, each joint 15 of the robot arm 10 includes a motor 23 and an encoder 25. The motor 23 generates power to move the corresponding arm 13. The encoder 25 detects an angular position of the motor 23.

The controller 30 controls the robot arm 10. The controller 30 may include a joint controller 31, a force controller 33, and a motion planner 35.

The joint controller 31 controls operation of the joints 15. More specifically, the joint controller 31 controls the joints 15 to operate a predetermined motion (check movement, described later referring to FIG. 6). The joint controller 31 receives encoder signals from each encoder 25, force control signals from the force controller 33, and motion control signals from the motion planner 35, and controls the joints 15 based on the received signals. The encoder signals are signals regarding the angular position of the motor 23. The force control signals are signals for controlling force/moment to be loaded on the shaft 91 and the hole 97 (described later). The motion control signals are signals regarding the motion of the robot arm 10. The joint controller 31 also outputs joint control signals to the motors 23, and outputs operation data to a user interface (UI) 51 via the motion planner 35. The joint control signals are signals regarding an operation of the motors 23. The operation data is data regarding a status of the operation of the motors 23.

The force controller 33 controls the force/moment to be loaded on the shaft 91 and the hole 97 via the joint controller 31 and the robot arm 10. The force controller 33 receives force/moment instructions 55 from the operating device 50 and sensor signals from the wrist sensor 21. The force/moment instructions 55 are instructions regarding the force/moment to be loaded on the shaft 91 and the hole 97 during the predetermined motion. The sensor signals represent signals regarding the force/moment detected by the wrist sensor 21. The force controller 33 determines force/moment to be loaded on the shaft 91 and the hole 97 during the predetermined motion based on the force/moment instructions 55, and outputs the force control signals to the joint controller 31 so that the joint controller 31 controls the joints 15 according to the determined force/moment. The force controller 33 also sets a force/moment threshold representing an allowable force/moment to be loaded on the shaft 91 and the hole 97 during the predetermined motion. The force controller 33 also determines timings to stop the predetermined motion based on the sensor signals from the wrist sensor 21, and outputs the force control signals to the joint controller 31 to stop the predetermined motion. The force controller 33 is an example of a claimed monitor.

The motion planner 35 controls position/angle of the shaft 91 via the joint controller 31 and the robot arm 10. The motion planner 35 receives position/angle instructions 53 from the operating device 50. The position/angle instructions 53 are instructions regarding the position/angle of the robot arm 10 during the predetermined motion. The motion planner 35 determines the predetermined motion based on the position/angle instructions 53 to output the motion control signals to the joint controller 31.

The operating device 50 operates the controller 30 according to inputs from an operator of the robot system 1. As shown in FIG. 2, the operating device 50 may include a UI 51 receiving the inputs from the operator. The operating device 50 stores the position/angle instructions 53 and the force/moment instructions 55. The position/angle instructions 53 and the force/moment instructions 55 may be set by the operator with the UI 51. The controller 30 and the operating device 50 are an example of a claimed controller.

The external device 70 receives the sensor signals from the wrist sensor 21 to estimate the actual clearance size between the shaft 91 and the body part 95. The external device 70 may include a determining portion 71. The determining portion 71 receives the sensor signals from the wrist sensor 21 to determine, i.e. estimate the clearance between the shaft 91 and the hole 97 of the body part 95. For example, the determining portion 71 determines the clearance based on a relation between each clearance size and the sensor signals from the wrist sensor 21 which is learned in advance (described later). The determining portion 71 may output the estimated clearance size to the outside of the external device 70. The determining portion 71 is an example of a claimed calculator.

As mentioned above with reference to FIG. 1, the robot system 1 holds the shaft 91 to conduct an insertion operation inserting the shaft 91 into the hole 97 of the body part 95. In other words, the robot system 1 installs the shaft 91 to the body part 95.

The shaft 91 and the body part 95 may be any mechanical parts. For example, the shaft 91 may be a gear shaft, and the body part 95 may be a gear body provided with a through-hole into which the gear shaft is inserted.

Note that shapes of the shaft 91 and the body part 95 are not limited to the shown example. The shaft 91 may be any shape as long as the shaft 91 has a pillar shape. For example, the shaft 91 may be a triangular pillar, a quadrangular pillar, a pentagonal pillar, or a hexagonal pillar. The body part 95 may be any shape as long as the body part 95 has a portion in which the shaft 91 is installed. In other words, the shaft 91 and the body part 95 may be any shape as long as the shaft 91 and the body part 95 may form a clearance therebetween.

In the above explanation, the wrist sensor 21 is provided between the gripper 17 and the joint 15 nearest to the gripper 17. Alternatively, the wrist sensor 21 may be provided on the joint 15 or the arm 13. Note that the clearance between the shaft 91 and the hole 97 can be detected more precisely if the wrist sensor 21 is provided nearer to the gripper 17 than the joint 15.

Further, the wrist sensor 21 may be any sensor as long as the wrist sensor 21 can detect the movement of the shaft 91. For example, the wrist sensor 21 may be an acceleration sensor, a gyro sensor, a position sensor, or a combination of them.

In the shown example, the robot system 1 inserts the shaft 91 into the hole 97, and also determines the clearance. However, the configuration for inserting the shaft 91 and determining the clearance is not limited to this example. For example, multiple robot systems may be applicable so that one robot system inserts the shaft 91 into the hole 97 and another robot system determines the clearance. As another example, an operator of the robot system 1 may conduct the insertion operation instead of the robot system 1.

Figure 3:
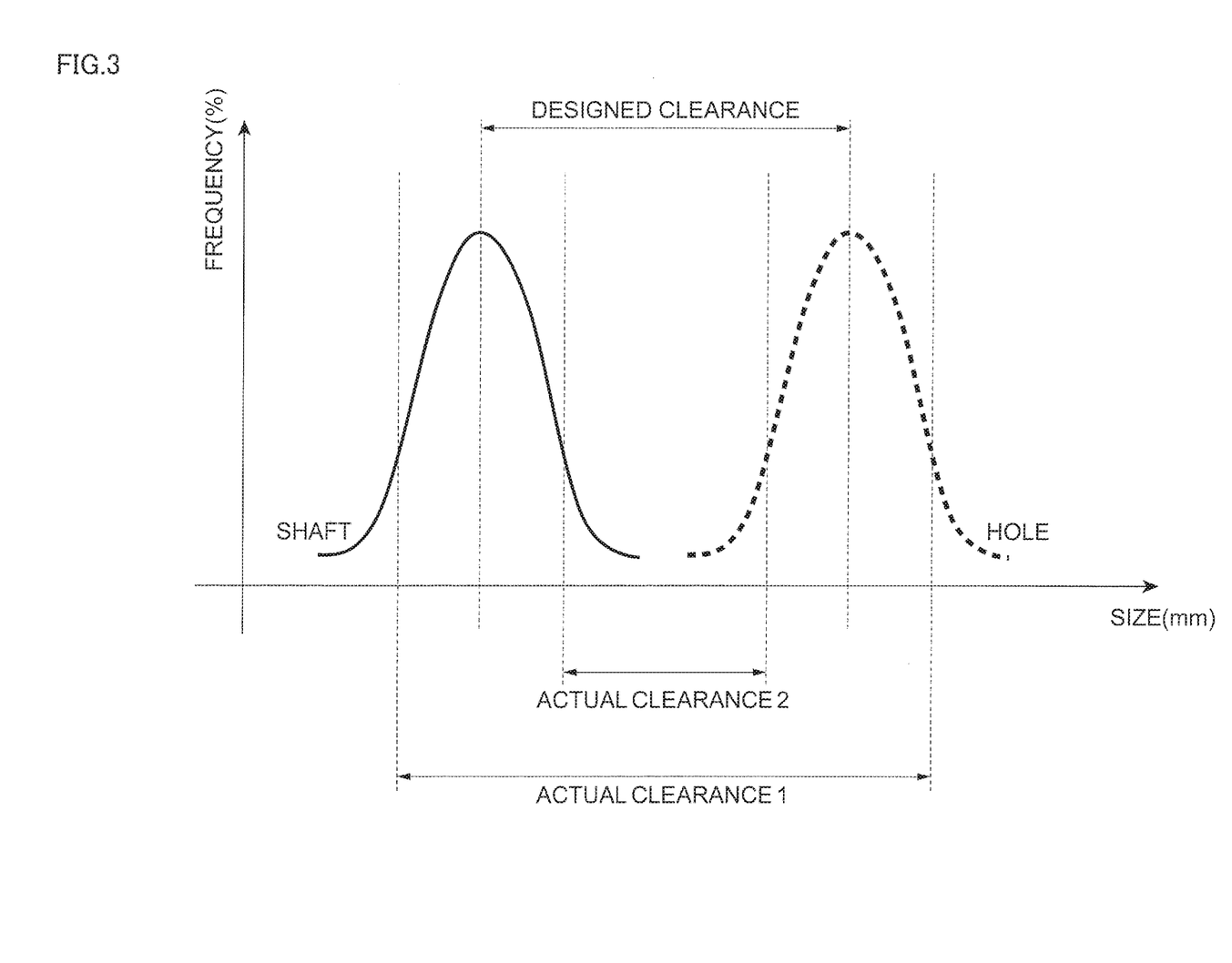
FIG. 3 depicts a relationship of the sizes of the shaft and the hole.

FIG. 3 depicts a relationship of the sizes of the shaft 91 and the hole 97. The horizontal axis indicates the size of the shaft 91 and the hole 97 (mm). The vertical axis indicates appearance frequency of respective sizes of the shaft 91 and the hole 97 (%).

Referring to FIG. 3, the clearance between the shaft 91 and the hole 97 will be explained in detail.

Mechanical parts are typically designed and manufactured with tolerance since it is unrealistic to design or manufacture zero tolerance mechanical parts. In the exemplary embodiment, the shaft 91 and the hole 97 are also manufactured with tolerance. Because of the tolerance, an actual clearance between the shaft 91 and the hole 97 can vary by every combination of the shaft 91 and the hole 97. For example, in FIG. 3, an actual clearance 1 is larger than a designed clearance, and an actual clearance 2 is smaller than the designed clearance. It is therefore desired to estimate the actual clearance at a manufacturing site, i.e. at the time of an assembly process of the work pieces 90.

To measure the clearance between the shaft 91 and the hole 97, a laser scanner is assumed to be applicable to the assembly process. It is, however, time consuming to measure the clearance of every combination of the shaft 91 and the hole 97 with the laser scanner.

For example, the measurement with the laser scanner requires a step for moving the robot arm 10 to a position out of a range to be irradiated with the laser after inserting the shaft 91 to the hole 97 with the robot arm 10. On the other hand, the robot system 1 according to the present embodiment does not require this step. This enables the robot system 1 to estimate the clearance between the shaft 91 and the hole 97 in a shorter time compared to the measurement with the laser scanner.

Figure 4:
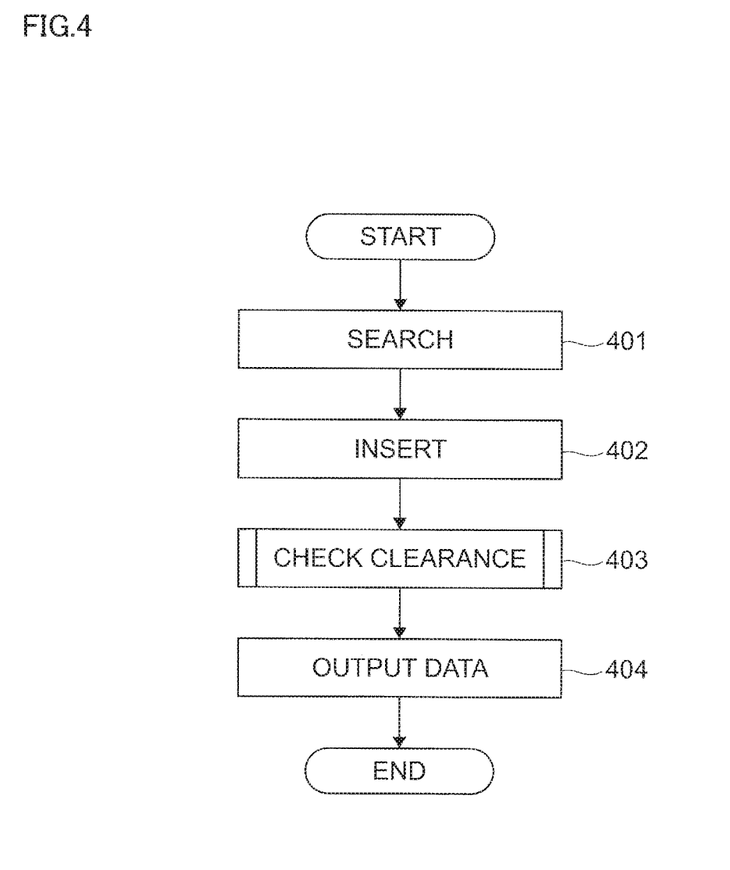
FIG. 4 is a flowchart of an operation of the robot system according to the exemplary embodiment.

FIG. 4 is a flowchart of an operation of the robot system 1 according to the exemplary embodiment. Referring to FIGS. 1 and 4, the operation of the robot system 1 will be explained. Note that in an initial state, the shaft 91 is held by the gripper 17 of the robot arm 10, and the body part 95 is placed on a predetermined position nearby the robot arm 10.

The controller 30, the operating device 50 and the robot arm 10 first perform a search process (step 401). The search process is a process to search for and detect a position of the hole 97 provided in the body part 95.

The controller 30, the operating device 50 and the robot arm 10 then perform an insertion process (step 402). The insertion process is a process to guide the shaft 91 by moving the gripper 17 to the detected position of the hole 97, and insert the shaft 91 into the hole 97.

The controller 30, the operating device 50, the robot arm 10, and the determining portion 71 then perform a clearance check process conducting the check movement (step 403, described later). The determining portion 71 then performs a data output process (step 404). The output data may include information on a result of the clearance check process.

Figure 5:
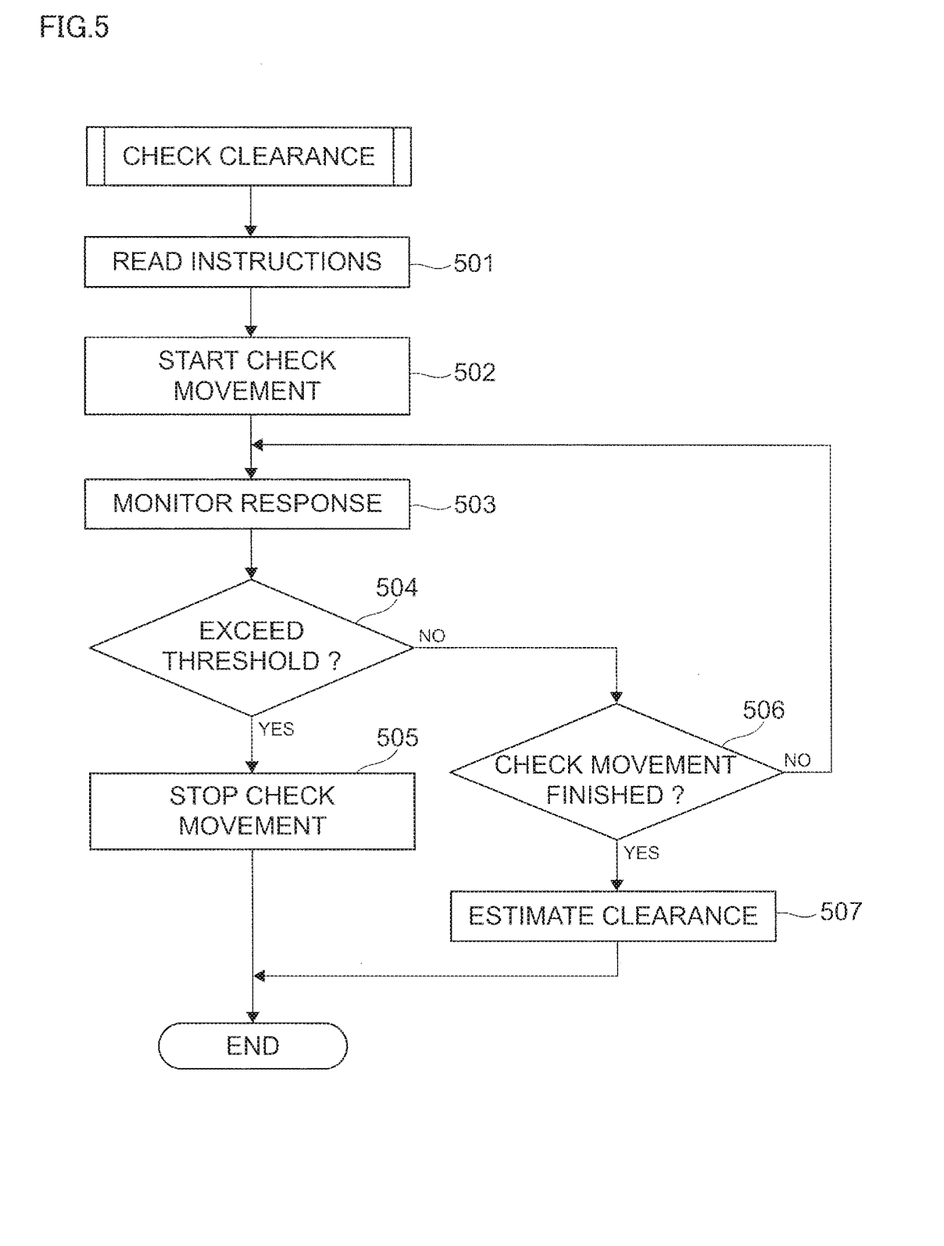
FIG. 5 is a flowchart of the clearance check process according to the exemplary embodiment.

FIG. 5 is a flowchart of the clearance check process according to the exemplary embodiment. Referring to FIG. 5, the clearance check process of the robot system 1 will be explained.

As shown in FIG. 5, in the clearance check process, the joint controller 31 first reads out the position/angle instructions 53 via the motion planner 35 and the force/moment instructions 55 via the force controller 33 (step 501). The joint controller 31, the motion planner 35, and the robot arm 10 then start a check movement according to the read instructions (step 502, described later). In other words, the joint controller 31 controls the joints 15 so that the robot arm 10 performs the check movement. During the check movement, the force controller 33 and the determining portion 71 monitor response to the check movement from the shaft 91 and the hole 97 (step 503). For example, the force controller 33 monitors whether the sensor signal from the wrist sensor 21 exceeds the force/moment threshold.

If the joint controller 31 detects that the sensor signal exceeds the threshold (Yes in step 504) based on the information from the force controller 33, the joint controller 31 stops the check movement (step 505) and the clearance check process ends.

If the sensor signal does not exceed the threshold (No in step 504), the joint controller 31 monitors whether the check movement is finished (step 506). If the check movement is finished (Yes in step 506), the determining portion 71 estimates the clearance (step 507) based on the monitored response data. In other words, the determining portion 71 calculates information on the clearance size between the shaft 91 and the hole 97.

As described above with reference to FIG. 4, the clearance check process (step 403) is conducted after the insertion process (step 402). During the insertion process and the clearance check process, the gripper 17 continues to hold the shaft 91. This enables to prevent a rotation of the shaft 91 which may occur if the gripper 17 releases the shaft 91 after the completion of the insertion process.

In the shown example, the controller 30 detects not only the position and the angle but also the force and the moment during the clearance check process. Further, the joint controller 31 stops the check movement if the force or the moment exceeds the threshold. This enables to prevent the shaft 91 and the body part 95 from being broken. If the shaft 91 and the body part 95 are fragile parts, the exceeded force or moment may cause defects and decrease the production efficiency.

Note that if the check movement is stopped, the joint controller 31 outputs the operation data to the UI 51 via the motion planner 35. Then the UI 51 may show information on the stop of the check movement to the operator of the robot system 100.

Figure 6:
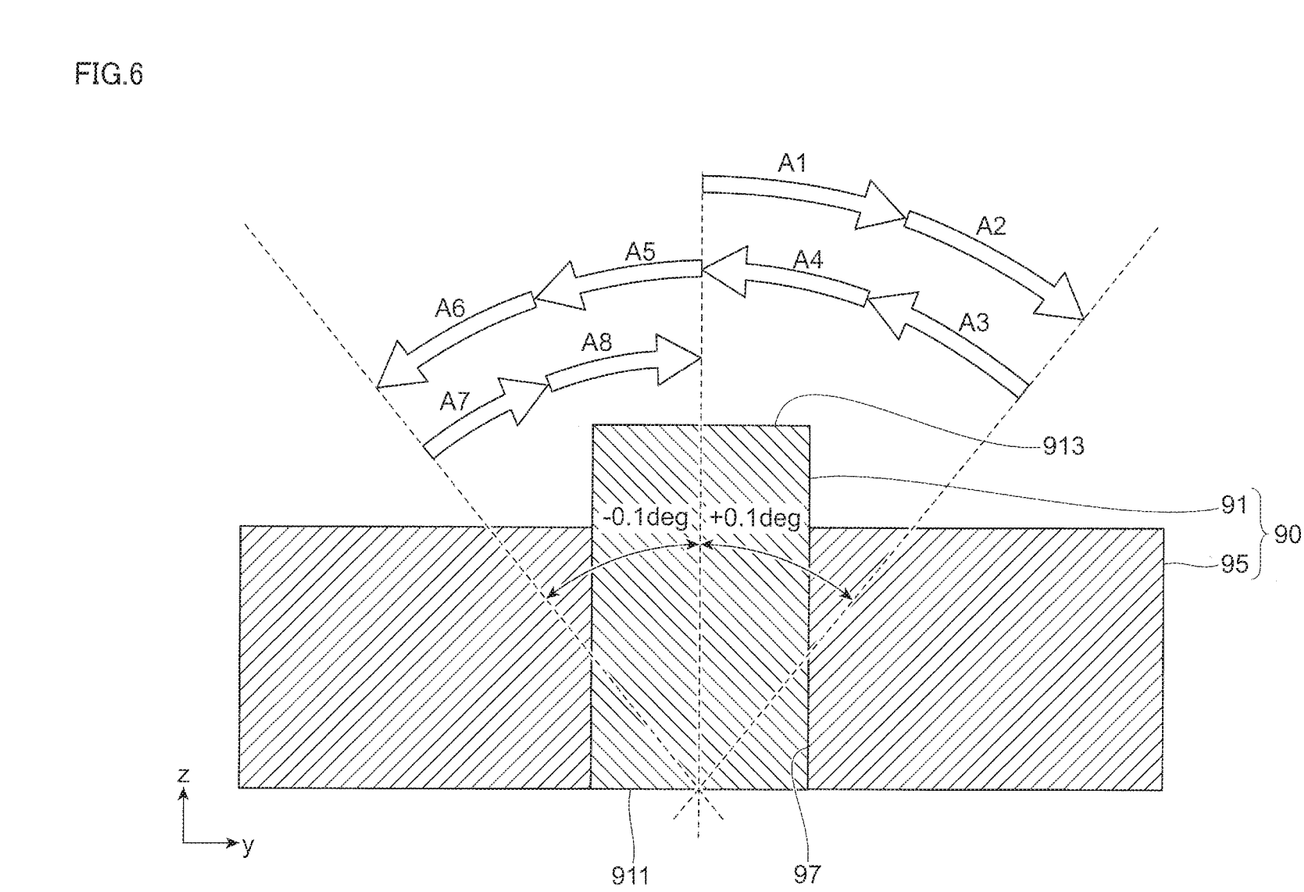
FIG. 6 depicts a schematic view of the check movement according to the exemplary embodiment.

FIG. 6 depicts a schematic view of the check movement according to the exemplary embodiment. Referring to FIG. 6, the operation of the check movement (predetermined motion) will be explained. In the check movement, the robot arm 10 oscillates the shaft 91 in the hole 97 to acquire response force/moment data by the wrist sensor 21, and the determining portion 71 estimates the clearance based on the acquired response force/moment data. The response force/moment data is data detected by the wrist sensor 21 with the check movement.

Note that the shaft 91 has two ends, i.e. the first end 911 and the second end 913. The first end 911 is in the hole 97. On the other hand, the second end 913 is out of the hole 97 and gripped by the gripper 17 (not shown in FIG. 6).

In the check movement, the gripper 17 holds and moves the second end 913 of the shaft 91 in a direction perpendicular to the axis of the shaft 91. In other words, the gripper 17 rotates the second end 913 around the first end 911 while maintaining the first end 911 within the hole 97.

In the shown example, the gripper 17 rotates the second end 913 by +/−0.1 degrees around both the x-axis and the y-axis (a roll angle and a pitch angle) twice sequentially. As shown in FIG. 6, the gripper 17 rotates the second end 913 toward one direction in two steps (refer to arrows A1 and A2). Then the gripper 17 rotates the second end 913 toward an opposing direction to the one direction in four steps (refer to arrows A3, A4, A5, and A6). Then the gripper 17 rotates the second end 913 toward the one direction in two steps (refer to arrows A7 and A8). The second end 913 is then placed on the original position.

While the gripper 17 conducts the rotation operation, the wrist sensor 21 acquires the response force/moment data and the force controller 33 tries to keep the force and moment control to zero. Note that the wrist sensor 21 acquires the response force/moment data over a period covering the rotation operation of the gripper 17. More specifically, the wrist sensor 21 starts to acquire the response force/moment data before the start of the rotation operation and ends it after the end of the rotation operation. For example, assuming that the rotation operation of the gripper 17 takes 1.28 seconds, the wrist sensor 21 acquires the response force/moment data for 1.32 seconds in 2 millisecond resolution with 40 millisecond cycle communications.

The above rotation operation of the gripper 17 is planned by the motion planner 35. The motion planner 35 determines the above rotation operation based on the position/angle instructions 53. For example, the position/angle instructions 53 may be prepared in advance to be read by the motion planner 35. The position/angle instructions 53 define the position and the angle of the gripper 17 in each step of the rotation operation based on the size of the shaft 91 and the hole 97.

As mentioned above, the gripper 17 rotates the second end 913 toward one direction in several steps (refer to the arrows A1 and A2 and the arrows A7 and A8), and toward the opposing direction in several steps (refer to the arrows A3 to A6). This can reduce an overload on the shaft 91 and the hole 97 (the body part 95).

Further, the response force/moment data acquired by the wrist sensor 21 is fed to the force controller 33. If the force controller 33 detects that the response force/moment data exceeds the threshold, the force controller 33 outputs the force control signal to the joint controller 31 to stop the rotation operation, i.e. to stop the clearance check process.

The response force/moment data acquired by the wrist sensor 21 is also fed to the determining portion 71. Based on the received response force/moment data, the determining portion 71 determines the actual clearance between the shaft 91 and the hole 97.

The result of the determination, i.e. the size of the actual clearance may be stored in the external device 70. Each result may be associated with information (e.g. lot IDs) by which the corresponding set of the shaft 91 and the hole 97 can be identified to ensure traceability.

The result of the determination is not limited to the size of the actual clearance. The result may be any information on the clearance. For example, the determining portion 71 may compare the response force/moment data with a clearance threshold representing an allowable limit of the actual clearance, to determine whether the response force/moment data is within the allowable limit. For example, the clearance threshold representing the allowable limit of the actual clearance may be set by the operator of the robot system 1. As another example, the clearance threshold representing the allowable limit of the actual clearance may be set using supervised machine learning.

Note that the clearance size can be estimated by using supervised machine learning. More specifically, using multiple sets of the shaft 91 and the hole 97 between which the clearance is already known, a relation between each clearance size and each response force/moment data is learned in advance by the determining portion 71. For example, in a case where the determining portion 71 recognizes a common pattern of the response force/moment data for different sets of the shaft 91 and the hole 97, the determining portion 71 may determine the same clearance size for the different sets of the shaft 91 and the hole 97 based on the relation learned in advance. By learning multiple common patterns for various clearance sizes in advance, the determining portion 71 may identify the clearance size from various learned clearance sizes. With the learned data, the determining portion 71 can estimate the clearance size based on the received response force/moment data. For example, the relation is learned as a model so that an estimated result of the clearance size can be acquired by inputting the response force/moment data to the model. Note that the method of the machine learning is not limited to a particular method.

Further, the check movement is not limited to the above example. The check movement may consist of any combination of motions in 6 degrees of freedom symmetrically or asymmetrically. Further, the check movement is not limited to the movement along the direction perpendicular to the axis of the shaft 91. The check movement may be a movement along a direction crossing the axis of the shaft 91 or a movement along the axis of the shaft 91.

Figure 7:
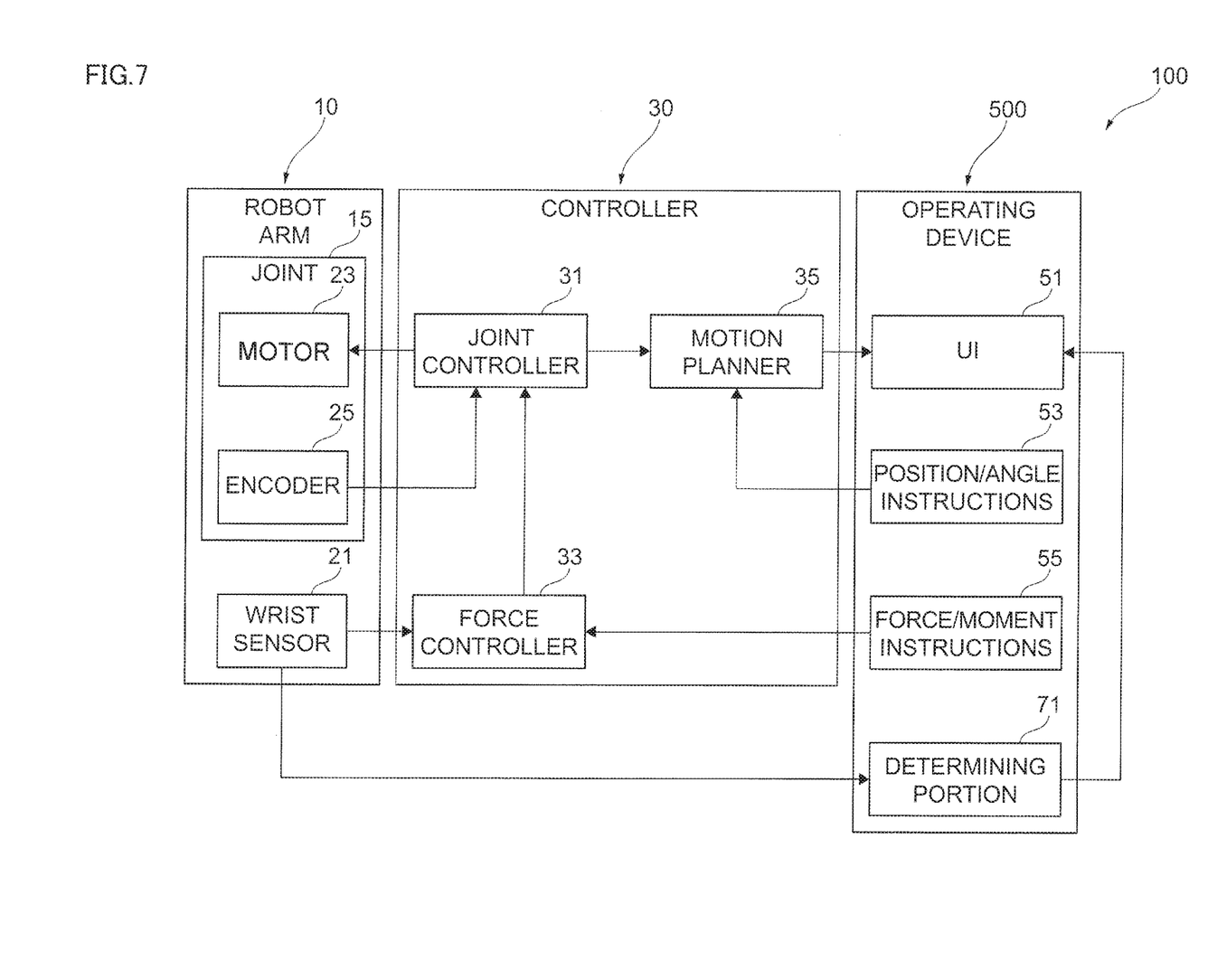
FIG. 7 depicts a schematic view of a configuration of a robot system according to an alternative embodiment.

FIG. 7 depicts a schematic view of a configuration of a robot system 100 according to an alternative embodiment. In FIG. 7, the same structures as those of the exemplary embodiment shown in FIG. 1 are denoted by the same reference numerals, and the detailed explanation thereof will be omitted.

As shown in FIG. 7, the robot system 100 may include the robot arm 10, the controller 30, and an operating device 500. Unlike the robot system 1 shown in FIG. 1, the robot system 100 may not include the external device 70, and the operating device 500 may include the determining portion 71.

The determining portion 71 in the operating device 500 determines the actual clearance between the shaft 91 and the hole 97 based on the received response force/moment data from the wrist sensor 21. The determining portion 71 may output the result (the actual clearance) to the UI 51. Then the UI 51 can show information on the actual clearance to the operator of the robot system 100.

Note that the operating device 500 may be provided at a remote place from the robot arm 10 and the controller 30, and may be connected via a network such as the Internet, Intranet, and a local area network (LAN). The operating device 500 may be integrated into the controller 30 in another embodiment.

Feeding of the response force/moment data from the wrist sensor 21 to the force controller 33 may be omitted. For example, if the shaft 91 and the body part 95 are not fragile parts, the check movement may not be required to be stopped. In this case, the response force/moment data may be fed only to the determining portion 71.

Figure 8:
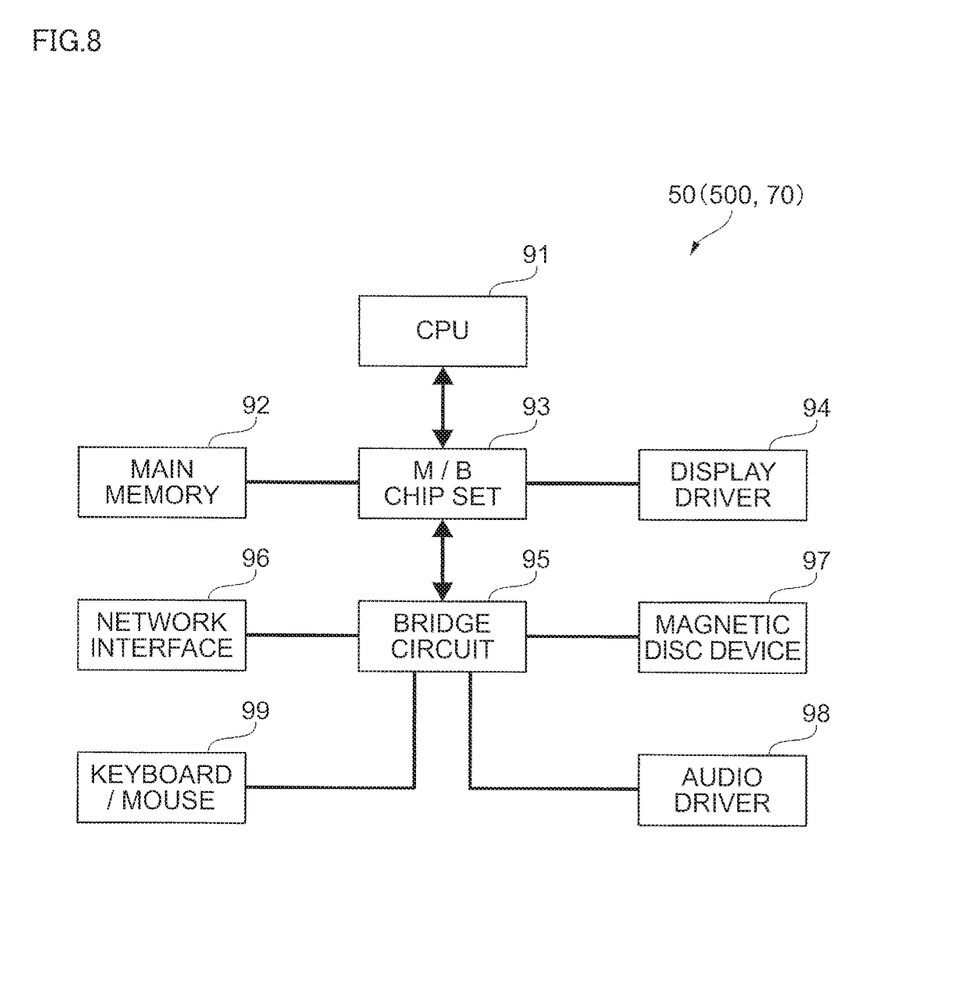
FIG. 8 depicts an example of a hardware configuration of the operating device and the external device according to the exemplary embodiments.

Referring to FIG. 8, there is shown an example of a hardware configuration of the operating device 50 (500) and the external device 70 in the exemplary embodiments. As shown in the figure, the operating device 50 (500) and the external device 70 may include a central processing unit (CPU) 91, a main memory 92 connected to the CPU 91 via a motherboard (M/B) chip set 93, and a display driver 94 connected to the CPU 91 via the same M/B chip set 93. A network interface 96, a magnetic disk device 97, an audio driver 98, and a keyboard/mouse 99 are also connected to the M/B chip set 93 via a bridge circuit 95.

In FIG. 8, the various configurational elements are connected via buses. For example, the CPU 91 and the M/B chip set 93, and the M/B chip set 93 and the main memory 92 are connected via CPU buses, respectively. Also, the M/B chip set 93 and the display driver 94 may be connected via an accelerated graphics port (AGP). However, when the display driver 94 includes a PCI express-compatible video card, the M/B chip set 93 and the video card are connected via a PCI express (PCIe) bus. Also, when the network interface 96 is connected to the bridge circuit 95, a PCI Express may be used for the connection, for example. For connecting the magnetic disk device 97 to the bridge circuit 95, a serial AT attachment (ATA), a parallel-transmission ATA, or peripheral components interconnect (PCI) may be used. For connecting the keyboard/mouse 99 to the bridge circuit 95, a universal serial bus (USB) may be used.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for inspecting a clearance size between a hole and an object inserted in the hole, comprising:
controlling a robot arm by performing a predetermined motion to move the object inserted in the hole;
monitoring a response to the predetermined motion from the hole and the object; and
calculating information on the clearance size between the hole and the object using the response to the predetermined motion, wherein calculating information on the clearance size includes estimating the clearance size by referring to a relation between the hole and the object clearance size and a response force/moment to the predetermined motion for the hole and the object clearance size, the relation being learned in advance.

2. The computer-implemented method according to claim 1, wherein controlling the robot arm includes:
controlling the robot arm by both (i) position and/or angle instructions to the robot arm, and (ii) force and/or moment instructions to the robot arm.

3. The computer-implemented method according to claim 1, wherein
the response to the predetermined motion is monitored by a sensor provided on the robot arm.

4. The computer-implemented method according to claim 1, wherein
the object comprises a shaft having a first end and a second end, the first end being inserted in the hole in the predetermined motion, and the second end being out of the hole in the predetermined motion, and
the second end of the shaft is oscillated in the predetermined motion.

5. The computer-implemented method according to claim 1, wherein
in a case where the monitored response to the predetermined motion exceeds a threshold, the predetermined motion is stopped.

6. A robot system comprising:
a robot arm configured to hold an object to insert the object in a hole;
a controller configured to control the robot arm so that the robot arm performs a predetermined motion to move the object inserted in the hole;
a monitor configured to monitor a response to the predetermined motion from the hole and the object; and
a calculator configured to calculate information on a clearance size between the hole and the object using the response to the predetermined motion, wherein the calculator estimates the clearance size by referring to a relation between the hole and the object clearance size and a response force/moment to the predetermined motion for the hole and the object clearance size, the relation being learned in advance.

7. The robot system according to claim 6, wherein the controller controls the robot arm by using both (i) position and/or angle instructions to the robot arm, and (ii) force and/or moment instructions to the robot arm.

8. The robot system according to claim 6, wherein
the object comprises a shaft having a first end and a second end, the first end being inserted in the hole in the predetermined motion, and the second end being out of the hole in the predetermined motion, and
the second end of the shaft is oscillated in the predetermined motion.

9. The robot system according to claim 6, wherein
in a case where the monitored response to the predetermined motion exceeds a threshold, the predetermined motion is stopped.

10. The robot system according to claim 6, wherein
the response to the predetermined motion is monitored by a sensor provided on the robot arm.

11. A computer program product for inspecting a clearance size between a hole and an object inserted in the hole, the computer program product comprising a non-transitory tangible storage device having program code embodied therewith, the program code being executable by a processor of a computer to perform a method, the method comprising:
controlling, by the processor, a robot arm so that the robot arm performs a predetermined motion to move the object inserted in the hole;
monitoring, by the processor, a response to the predetermined motion from the hole and the object; and
calculating, by the processor, information on the clearance size between the hole and the object using the response to the predetermined motion, wherein calculating, by the processor, information on the clearance size includes estimating the clearance size by referring to a relation between the hole and the object clearance size and a response force/moment to the predetermined motion for the hole and the object clearance size, the relation being learned in advance.

12. The computer program product according to claim 11, wherein the method further comprises:
controlling, by the processor, the robot arm by using both (i) position and/or angle instructions to the robot arm, and (ii) force and/or moment instructions to the robot arm.

13. The computer program product according to claim 11, wherein
the object comprises a shaft having a first end and a second end, the first end being inserted in the hole in the predetermined motion, and the second end being out of the hole in the predetermined motion, and
the second end of the shaft is oscillated in the predetermined motion.

14. The computer program product according to claim 11, wherein
in a case where the monitored response to the predetermined motion exceeds a threshold, the predetermined motion is stopped.

15. The computer program product according to claim 11, wherein
the response to the predetermined motion is monitored by a sensor provided on the robot arm.

* * * * *